United States Patent [19]

Winters

[11] 4,404,405

[45] Sep. 13, 1983

[54] PROCESS FOR THE PREPARATION OF POLYETHYLENE POLYAMINES

[75] Inventor: John R. Winters, South Charleston, W. Va.

[73] Assignee: Union Carbide Corporation, Danbury, Conn.

[21] Appl. No.: 307,243

[22] Filed: Sep. 30, 1981

[51] Int. Cl.$^3$ ............... C07C 85/04; C07C 85/06; C07C 89/02

[52] U.S. Cl. ............... 564/482; 564/475; 564/477; 564/479; 564/480; 564/511; 564/512

[58] Field of Search ............ 564/477, 480, 475, 479, 564/482

[56] References Cited

U.S. PATENT DOCUMENTS

| | | | |
|---|---|---|---|
| 2,196,554 | 4/1940 | Guinot | 260/584 |
| 3,068,290 | 12/1962 | Lichtenberger et al. | 260/585 |
| 3,270,059 | 8/1966 | Winderl et al. | 260/583 |
| 3,520,933 | 7/1970 | Adam et al. | 260/585 |
| 3,697,598 | 10/1972 | Weibull et al. | 260/584 |
| 3,723,530 | 3/1973 | Goetze et al. | 260/584 R |
| 3,766,184 | 10/1973 | Johansson et al. | 260/268 |
| 4,014,933 | 3/1977 | Boettger et al. | 260/563 |
| 4,111,840 | 9/1978 | Best | 252/432 |
| 4,123,462 | 10/1978 | Best | 260/585 B |
| 4,153,581 | 5/1979 | Habermann | 252/472 |
| 4,209,424 | 6/1980 | Le Goff et al. | 252/474 |

FOREIGN PATENT DOCUMENTS 1950604 4/1971 Fed. Rep. of Germany .
44-12723 5/1967 Japan .

OTHER PUBLICATIONS

Shuichi Yamashita, Ethylene Amines-Their Properties, Uses and Manufacturing Processes, Chemical Economy & Engineering Review, vol. 3, No. 9, pp. 39-43 (1971).
Michael Arne, Process Economics Program, "Alkyl Amines", Private Report, No. 138, Stamford Research Institute, Mar. 81.

*Primary Examiner*—John Doll
*Attorney, Agent, or Firm*—Jean B. Mauro

[57] ABSTRACT

There is disclosed a continuous process for making polyethylene polyamines such as diethylenetriamine, triethylenetetramine, etc. comprising the reaction of ethylene oxide with ammonia to produce a mixture of alkanolamines, the amination of the alkanolamines to ethyleneamines, and the reaction of at least a portion of the ethyleneamines thus produced with ethylene dichloride optionally in the presence of ammonia and/or water.

14 Claims, 1 Drawing Figure

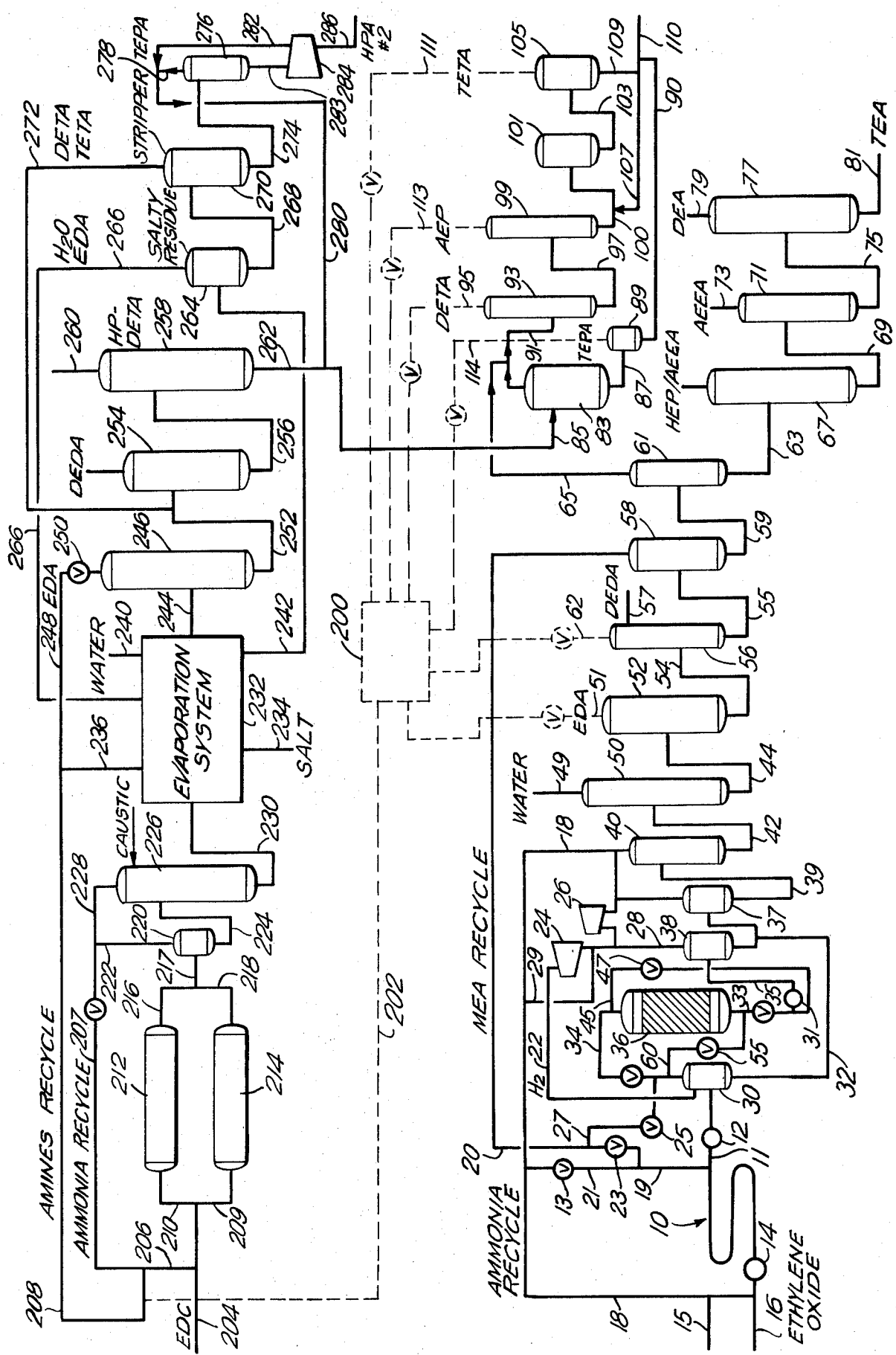

4,404,405

PROCESS FOR THE PREPARATION OF POLYETHYLENE POLYAMINES

BRIEF SUMMARY OF THE INVENTION

1. Technical Field

The invention relates to the manufacture of polyethylene polyamines which comprises a multiplicity of steps but which in the sum total constitutes the reaction of ethylene dichloride, ammonia and ethylene oxide. The process of this invention involves the continuous manufacture of ethyleneamines starting from the reaction of ethylene oxide with ammonia to produce a mixture of alkanolamines and the conversion of the alkanolamines by amination to ethyleneamines. The ethyleneamines so formed are thereafter reacted with ethylene dichloride, optionally in the presence of ammonia, to produce as a consequence thereof a variety of higher molecular weight ethyleneamines having an increase in molecular weight by at least one ethylene moiety, herein called polyethylene polyamines.

2. Background Art

In a private report by the Process Economics Program, Report No. 138, entitled "Alkyl Amines", by Michael Arne, SRI International, dated March 1981, there are sections which covers the production of ethyleneamines from ethylene dichloride and ethyleneamines from monoethanolamine (see pps. 43–107, 114, 115, 116 and 117). The author considered a substantial collection of the prior art relating to the conversion of monoethanolamine to ethylenediamine, in particular, as well as other ethyleneamines and considered a substantial collection of the prior art in relation to the reaction of ethylene dichloride with ammonia to also produce ethylenediamine, in particular.

At page 81 of the Arne article, we find the following statement regarding the process for making ethyleneamines from monoethanolamine and its advantages and disadvantages vis-a-vis the ammonia-ethylene dichloride process for making ethyleneamines:

"Because of environmental problems involving the formation of vinyl chloride and sodium chloride contaminated with organics, considerable attention has been given in recent years to an alternative to the ethylene dichloride route for the production of ethyleneamines. Currently in Europe, BASF and Berol produce ethyleneamines from monoethanolamine and ammonia, and Union Carbide has announced a plant expansion based on the same. This route has the advantage of virtually eliminating the environmental problems associated with the ethylene dichloride process. However, it has the disadvantage of producing only small quantities of polyethylene polyamines, producing instead substantial amounts of less valuable piperazine and substituted piperazines."

By comparing Table 5.10 at page 77 with Table 6.7 of the Arne Report (p. 103), we find that ethyleneamines produced from monoethanolamine have a production cost of 76.5¢ per pound whereas Table 5.10 at page 77 shows the ethyleneamines production cost as obtained by the ethylene dichloride-ammonia process is 72.5¢ per pound. However, the total capital investment for a comparable plant making ethyleneamines from ethylene dichloride is 50.8 million dollars as compared with a capital investment for an ethyleneamines plant from monoethanolamine of 27.8 million dollars. At page 8 of the Arne Report, we have the following statement made:

"A comparison of Cases A and C shows that the ethylene dichloride route has a higher capital investment and higher utilities costs. The monoethanolamine route has a considerably higher raw materials cost. Product values are similar. However, the ethylene dichloride process produces a higher proportion of higher priced polyamines, e.g., DETA, TETA, TEPA, as opposed to the less valuable substituted piperazines which make up a substantial portion of the product mix for the monoethanolamine process.

The environmental difficulties associated with the ethylene dichloride route include side reaction to vinyl chloride and disposal of organics contaminated sodium chloride. Because of this it seems likely that future capacity will use the monoethanolamine route. This route has the disadvantage of not producing polyamines but work is being done on commercializing a means of producing polyamines from monoethanolamine and ethylenediamine. Currently, it seems that as total demand for ethyleneamines increases, ethylenediamine demand will be met by new capacity from monoethanolamine, with polyamines demand being met by shifting production in existing ethylene dichloride plants toward more polyamines."

In attempting to reconcile the last comments about meeting polyamines demands by shifting production in existing ethylene dichloride plants towards more polyamines, it is believed that the author was stating that this will be accomplished by reducing the ratio of ammonia to ethylene dichloride used in the reaction. This will result in the formation of a higher proportion of higher polyethylene polyamines. In any event, it would not make much sense for one who is producing ethyleneamines by the ethylene dichloride process at a production cost lower than could be achieved by the monoethanolamine process to thereafter take the ethyleneamines from the monoethanolamine process and incorporate them into the ethylene dichloride process to produce increased amounts of polyethylene polyamine.

There is described in copending application Ser. No. 307,215 a continuous process for the manufacture of ethtylenediamine comprising the reaction of ethylene oxide with ammonia to produce a mixture of alkanolamines and the conversion of the alkanolamines by amination to ethylenediamine and other products. The process described in said application is the first to economically react ammonia and ethylene oxide directly to ethanolamines and without any significant loss in the energy generated in making the ethanolamines, convert the same into ethyleneamines. Heretofore, such ethanolamines were isolated products which had to be brought up to reaction temperature and pressure prior to their utilization in reactions with ammonia in order to effect the production of ethyleneamines. This increases the cost of the manufacture of ethyleneamines by a substantial margin and is, without question, a significant factor reflected in the data of the Arne Report recited above in respect to the production cost of ethyleneamines.

Arne considered a substantial collection of the prior art relating to the conversion of monoethnolamine to, in particular, ethylenediamine. For example, the author considers Lichtenberger et al., U.S. Pat. No. 3,068,290, patented Dec. 11, 1962, who describe the reaction of ammonia and monoethanolamine over a nickel/magnesium oxide catalyst to give ethylenediamine; Winderl et al., U.S. Pat. No. 3,270,059, patented Aug. 30, 1966, who describe the reaction of monoethanolamine and ammonia in the presence of hydrogen over a cobalt/nickel catalyst at 150°–300° C. and 200 atm.; Johansson et al., U.S. Pat. No. 3,766,184, patented Oct. 16, 1973, who describe the reaction of ammonia and monoethanolamine to give ethylenediamine; Adam et al., U.S. Pat. No. 3,520,933, patented July 21, 1970, who describe the reaction between ammonia and monoethanolamine over a cobalt/nickel/copper/silver catalyst in the presence of hydrogen to give ethylenediamine; Corr et al., French Pat. No. 2,065,046, published July 23, 1971, who describe the production of ethylenediamine from monoethanolamine and ammonia by reaction over a cobalt catalyst containing phosphorus pentoxide and boric oxide; Boettger et al., U.S. Pat. No. 4,014,933, patented Mar. 29, 1977, who describe the reaction of ammonia and monoethanolamine over a cobalt/nickel catalyst in the presence of hydrogen; Best, U.S. Pat. No. 4,123,462, patented Oct. 31, 1978, who describes the reaction of ammonia with monoethanolamine or a mixture of alkanolamines such as one which contains 90% by weight of monoethanolamine, 7% by weight of diethanolamine and 3 weight percent of triethanolamine, in the presence of a nickel-rhenium supported catalyst; Habermann, U.S. Pat. No. 4,153,581, patented May 8, 1979, who describes the reaction of ammonia and monoethanolamine, in a mole ratio of 7/1, in the presence of a cobalt/copper/zinc oxide catalyst at 1500 psia to produce ethylenediamine; and LeGoff et al., U.S. Pat. No. 4,209,424, patented June 24, 1980, who produce ethylenediamine from monoethanolamine and ammonia over a nickel catalyst utilizing a rhodium promoter.

The significance of the aforementioned report by Arne is its evaluation of the prior art and its interpretation, on the basis of his evaluation of the prior art, of a process for the manufacture of ethylenediamine from monoethanolamine and ammonia. According to Arne, this route has the advantage of virtually eliminating the environmental problems associated with the ethylene dichloride process. In characterizing the process, Arne states that: "It has the disadvantage of producing only small quantities of polyethylene polyamines, producing instead substantial amounts of less valuable piperazine and substituted piperazines." What this means is that according to Arne, polyethylene polyamines are regarded to be valuable products and the piperazines are not regarded to be valuable products because the market for the piperazines is not large enough for the capacity existing for producing the same.

According to Arne, a desirable process for the manufacture of ethyleneamines would be one which would produce substantially smaller amounts of the piperazines and larger amounts of the various polyethylene polyamines.

In the analysis of the prior art that Arne relied upon, some interesting factors which induce the manufacture of the piperazines are revealed. For example, U.S. Pat. No. 3,766,184 reveals in example 10 that when diethanolamine was reacted with ammonia and water at 225° C. and 230 atm. in the presence of hydrogen gas and 7 grams of the reduced catalyst in tablet form comprising 3 to 4% each of nickel oxide, cobalt oxide and iron oxide, the remainder being aluminum oxide, 26% of the diethanolamine had been converted of which 49% had formed aminoethylethanolamine, 36% formed piperazine, and 8% formed ethylenediamine. After 5 hours of reaction, the example shows that 82% of the diethanolamine had been converted, of which 16% had been aminated to aminoethylethanolamine, 60% to piperazine, and 10% to ethylenediamine. Thus with diethanolamine, considerably more piperazine was formed than ethylenediamine. This should be contrasted with example 17 of the same patent which reacted ammonia with monoethanolamine in the presence of water and obtained ethylenediamine as 60% of the yield of product, piperazine as 12% of the product yield, aminoethylpiperazine as 2% of the product yield and hydroxyethylpiperazine as 2% of the product yield. When diethanolamine is combined with monoethanolamine as a reactant in the process of that patent, we see from example 11 that the conversion to piperazine is intermediate of those conversions obtained in examples 10 and 17, suggesting that the presence of diethanolamine was a major factor for this increase in the conversion to the unwanted piperazine.

U.S. Pat. No. 4,014,933, in example 5, also demonstrates the reaction of ammonia with diethanolamine. In that example, the patentees obtained a product composition comprising 4% ethylenediamine, 22% of piperazine, 17% of aminoethylethanolamine, and 54% of unreacted diethanolamine. Essentially the same results can be seen in example 8 of German published application No. 1,950,604, published Apr. 22, 1971.

The aforementioned examples which clearly demonstrate the propensity of diethanolamine to react with ammonia to produce a disproportionate amount of piperazines is further demonstrated in U.S. Pat. No. 3,766,184. By comparing examples 11 and 17 of the patent, we find that the presence of diethanolamine and triethanolamine in the reaction feed, as demonstrated in example 11, contribute to the formation of a disproportionate amount of piperazine. It should be noted in the case of example 17 that the feed was ammonia with monoethanolamine and the amount of the piperazines which were formed constituted essentially 1/10th the amount of the ethylenediamines formed. In example 11 the piperazines which were formed constituted 1/5th of the amount of ethylenediamine which was formed. However, in example 17, the process was operated in such a manner as to favor the formation of piperazine; note that the monoethanolamine conversion in example 17 was 55% which indicates a longer reaction time thus favoring high conversions which "leads to lower selectivity to the desired ethylenediamine and to more of the undesirable piperazine", see Arne, pg. 83, supra.

This would suggest that the presence of diethanolamine and/or triethanolamine in the feed along with monoethanolamine contributes to the formation of an amount of piperazine which exceeds that which would be obtainable from monoethanolamine alone. It also suggests that the amount of the piperazines formed exceeds that amount which the amount of diethanolamine and/or triethanolamine, per se, would form under the reaction conditions employed. This being the case, it is logical to assume that diethanolamine and/or triethanolamine are in some manner reacting with monoethanolamine or inducing the unfavorable reaction of monoethanolamine so as to form increased amounts of the unwanted piperazines.

The foregoing analysis also suggests that the prior art's manufacture of alkyleneamines from monoethanolamine reaction with ammonia is sound. If one were to utilize a reaction feed of monoethanolamine combined with diethanolamine and/or triethanolamine, more of the unwanted piperazines would be produced and this would constitute an economic loss.

However, the use of monoethanolamine alone is not without its disadvantages. It is known that monoethanolamine is formed by the reaction of ammonia and ethylene oxide and the product of that reaction constitutes a mixture of monoethanolamine, diethanolamine and triethanolamine. If monoethanolamine has to be isolated before it is utilized in the manufacture of the alkyleneamines, it means that the monoethanolamine must be distilled from its admixture and this adds to the cost of the monoethanolamine. Moreover, such monoethanolamine, when recovered, is brought to normal room temperature and when it is subsequently utilized in the formation of the ethyleneamines, it has to be reheated and pressurized to the conditions utilized for the manufacture of the ethyleneamines. Consequently, there is a considerable energy cost involved in the effective utilization of monoethanolamine per se. It should also be appreciated that the ammonia which is utilized in the reaction to produce the monoethanolamine is not directly available for the reaction to produce the alkyleneamines unless it is subjected to the same treatment of heating and repressurization as is the monoethanolamine.

The Arne Report discusses a number of problems associated with the ethylene dichloride process for making ethyleneamines, in the following manner:

"The amount of vinyl chloride allowable in the system is important in determining the fraction of recycle ammonia which must be scrubbed. Because data is sketchy in this regard, 1.5 weight percent of the flow to the first enriching column was assumed.

The material required for the reactor is titanium. Any equipment in contact with caustic or sodium chloride solutions is 316 stainless steel. Long term storage for three or four months causes darkening and iron pickup from carbon steel (456156). Therefore, storage tanks are aluminum. All other equipment is carbon steel." (See pages 69, 70).

At page 50 of the Arne Report, we find the following comment about the presence of vinyl chloride in the ethylene dichloride-ammonia reaction system:

"Production of vinyl chloride in the reactor causes complications as build up of vinyl chloride in the system leads to polymerization and subsequent blockage of columns and other equipment (456022). This is dealt with by scrubbing anhydrous ammonia containing vinyl chloride with water, with the aqueous ammonia formed being recycled to the process, while the vinyl chloride vapor is sent to waste disposal."

According to Arne, at pages 43 and 44, the reaction between ethylene dichloride and ammonia results in the formation of amine hydrochlorides which are thereafter treated with caustic soda to liberate the amine. As a consequence there is a substantial amount of salt which has to be removed from the reaction system. As quoted previously, the salt is contaminated with organics and such constitutes a difficult product to separate and dispose of. Thus, the process for making ethyleneamines from ethylene dichloride is subject to substantial environmental problems.

At page 45 of Arne, a general discussion of the operation of the ethylene dichloride-ammonia reaction system is set forth, as follows:

"The product distribution can be controlled by the $NH_3$ EDC feed ratio and by recycling one or more product amines to the reactor. Selectivity to EDA is increased with higher $NH_3/EDA$ ratios, higher temperature and pressure, and lower residence time in the reactor. The highest yield EDA reported is 90.9 wt. percent at a temperature of 170° C., and $NH_3/EDC$ molar ratio of 40.1/1 and a residence time of 2.8 min. Selectivity to polyamines is increased with lower $NH_3/EDC$ ratios, lower temperature and pressure, and a longer residence time in the reactor. Recycling unwanted product amines to the reactor also increases the relative production of polyamines. It is possible to recycle EDA and DETA to extinction, accordiang to Reference 456143. This reference mentions that the reaction of ammonia and EDC proceeds stepwise, with $\beta$-chloroethylamine being formed as an intermediate. The product amines are recycled to the reactor at a point where the concentration of $\beta$-chloroethylamine is at a maximum."

An analysis of the production costs for making ethyleneamines from the ethylene dichloride-ammonia reaction establishes that one of the prime factors, according to Arne, is the raw material cost. As shown at page 77 of the Arne Report, we find that ethylene dichloride is priced at 13.8¢ per pound. At Table 6.7 of the Arne Report, at page 103, where the production costs for making ethyleneamines from monoethanolamine is discussed, the cost for monoethanolamine is 52.5¢ per pound, a raw material cost which is 38.7¢ per pound higher than the ethylene dichloride cost. That statement does not take into consideration the usage of either one of ethylene dichloride or monoethanolamine in their respective processes but it does reflect a simple characterization which reflects the obvious importance that raw material costs play in each of the processes vis-a-vis their production costs.

The last point with respect to production costs demonstrates the criticality of making monoethanolamines at a low enough price so that its conversion to ethyleneamines is relatively small as compared to the process of making ethyleneamines by the ethylene dichloride-ammonia reaction. There is clearly, from these figures, a need for a process for making monoethanolamine from ethylene oxide which would not result in pressure reductions and temperature losses so that the eventual ethyleneamines which are produced would be in essence based upon the fundamental costs of ethylene oxide and ammonia rather than the cost of monoethanolamine. It is by such a process that one could instantaneously reduce the cost of making ethyleneamines as reflected in the Arne Report so that the ethyleneamines produced from monoethanolamine can be made at a production cost which is less than they could be made from the ethylene dichloride-ammonia process.

At page 8 of the Arne Report, Arne speculates that part of the "polyamines demand" will be "met by shifting production in existing ethylene dichloride plants toward more polyamines." This is interpreted to mean that the polyamines demand will be met by reducing the ratio of ammonia to ethylene dichloride. It is well known that this procedure can be employed for increasing the production of polyalkylene polyamines in the ethylene dichloride-ammonia reaction, see e.g. Yamashita, Chemical Economy & Engineering Review, September 1971, Vol. 3, No. 9 (No. 41) pages 39–43, especially at page 41; Murthy, J. Sci. Industr. Res., Vol. 17A, July 1958, pages 276–279, especially at page 277. Japanese Kokoku 6912723 describes the effect of recycling ethylenediamine and other alkylene polyamines in the conventional manufacture of ethyleneamines by the reaction of ammonia with ethylene dichloride in order to increase the concentration of polyethylene polyamines. The publication also mentions that by increasing or decreasing the molar ratio of ethylene dichloride to ammonia that one can control the amount of higher molecular weight alkylene polyamines as relative to the amount of the lower molecular weight components such as ethylenediamine.

DISCLOSURE OF INVENTION

There is described herein a continuous process for the manufacture of polyethylene polyamines which comprises providing a continuous homogeneous fluid stream under pressure, which stream comprises ammonia, monoethanolamine, diethanolamine and triethanolamine as produced by direct reaction of ethylene oxide and ammonia. The stream contains ammonia in an amount such that the number of moles thereof substantially exceeds the molar concentration of alcoholic hydroxyl groups present in the stream. The process also involves providing a continuous recycle stream consisting essentially of monoethanolamine and provides for an amination zone comprising a solid amination catalyst and a separation zone for separating monoethanolamine from the amination product stream removed from the amination zone. The monoethanolamine which is separated from the amination product stream forms the aforesaid recycle stream. The recycle stream is fed under pressure to the amination zone by combining it with the aforesaid fluid stream to form a continuous amination feed stream which is under pressure. This amination feed stream is supplied to the amination zone which is maintained at a superatmospheric pressure but sufficiently below the pressure of the amination feed stream to assure flow thereof through the amination zone and to form an amination product stream containing ethyleneamines therein. The ethyleneamines are continuously recovered from the aforesaid amination product stream. The amination feed stream provided contains at least 70 weight percent of monoethanolamine based on the weight of the ethanolamines contained therein. The moles of ammonia in the amination feed stream exceeds the molar concentration of alcoholic hydroxyl groups in said amination feed stream. The amination feed stream also contains at least a 5% increase in the concentration of monoethanolamine over that which is contained in the aforesaid homogeneous fluid stream. At least a portion of the ethyleneamines which are recovered from the aforesaid amination product stream is fed to a polyamines reaction zone wherein the ethyleneamines are caused to react with ethylene dichloride therein, optionally in the presence of at least one of ammonia and water, to produce higher molecular weight polyethylene polamines per se or as the hydrochloride, which polyethylene polyamines are higher in molecular weight than the said ethyleneamines by at least an ethylene moiety, and said polyethylene polyamines are recovered.

The process of this invention provides a number of advantages for the production of polyethylene polyamines of higher molecular weight over the processes which would produce similar products by either reducing the amount of ammonia present in the reaction of ammonia and ethylene dichloride or by recycling ethyleneamines which are produced in the reaction zone comprising ethylene dichloride and ammonia. First of all, the ethyleneamines which are reacted with ethylene dichloride, optionally in the presence of at least one of ammonia and water, of the instant invention are cheaper materials to produce than the corresponding materials which would be produced by the reaction of ethylene dichloride and ammonia. Furthermore, by supplying ethyleneamines which are basically derived from the reaction of ethylene oxide and ammonia, one introduces to the overall process more flexibility in respect to the product mix that is obtained. There is limited flexibility in the process of making higher molecular weight polyethylene polyamines by reducing the amount of ammonia versus the amount of ethylene dichloride employed or by recycling ethyleneamines to the ethylene dichloride-ammonia reaction. The process of this invention allows the production of more of the polyethylene polyamines than can be produced by the ethylene dichloride-ammonia process whether operated by reducing the ammonia reactant or by recycling ethylene amines. Furthermore, since the ethyleneamines initially derived from ethylene oxide are produced by a process which does not in any way utilize chlorine or require the post treatment with caustic, resulting in the formation of the substantial amounts of sodium chloride, the process of this invention results in the formation of less pounds of sodium chloride per pound of the amines produced. Another advantage of the process of this invention is that it will generate less pounds of vinyl chloride for each pound of amines produced as compared to the processes of the conventional ethylene dichloride-ammonia reaction system. As pointed out previously the process of this invention allows one to obtain and utilize ethyleneamines which are initially derived from ethylene oxide and not the expensive monoethanolamine. Consequently, the process of this invention achieves lowest cost investment and the lowest raw material prices resulting in a reduction in the cost of the production of higher molecular weight polyethylene polyamine than would heretofore be achieved.

The process of this invention achieves a production cost advantage of at least 20% over the production cost of producing ethyleneamines by the ethylene dichloride-ammonia process. Giving proper credits for piperazines, the process of this invention gives a substantially greater return on investment and net income, even on an after tax basis, than the ethylene dichloride-ammonia process.

DETAILS OF THE INVENTION

Reaction Between Ethylene Oxide and Ammonia to Form Alkanolamines

The process which may be employed to provide a product stream of alkanolamines by the reaction of ethylene oxide and ammonia, viz. the aforementioned continuous homogeneous fluid stream, may be any one of the processes described in the prior art which involve the reaction of ethylene oxide with ammonia to produce a mixture of monoethanolamine, diethanolamine and triethanolamine. A desirable process from the standpoint of this invention is one which produces a mixture in which monoethanolamine is present in amounts greater than 50 weight percent of the total concentration of alkanolamines. Illustrative of such processes are those described in U.S. Pat. No. 2,196,554, U.S. Pat. No. 3,697,598, and U.S. Pat. No. 3,723,530.

The process in U.S. Pat. No. 2,196,554 to Guinot involves preparing monohydroxylalkylamines in yields of 90%–95% by reacting at least 30 parts by weight of ammonia with 1 part of alkylene oxide in a liquid phase reaction. Relatively dilute aqueous ammonia solutions are employed and the patent discloses that steam generated during concentration of the reaction product mixture is used for heating subsequent reaction product mixtures to separate ammonia gas therefrom, thus reducing the heat energy requirements for the process. In the practice of the instant invention, when utilizing the reaction of this patent it will not be necessary to separate the ammonia gas from the product mixture since ammonia gas will be utilized in the amination step resulting in the formation of the alkyleneamines.

Another process for preparing alkanolamines with extremely high yields of monoalkanolamines and only small amounts of the di- and trialkanolamines by reacting alkylene oxides with large excess amounts of ammonia in a liquid phase reaction system is disclosed in U.S. Pat. No. 3,697,598 to Weibull et al. The relative molar ratio of ammonia to alkylene oxide used in the process is within the range of 10:1 to 80:1 with the reaction being carried out in the presence of a cation exchange resin catalyst. The process of this patent is described as being a continuous process which is capable of being run isothermally or, preferably, adiabatically at temperatures in the range of 20° C. to 250° C. when pressures are employed that are high enough to keep the reactants and reaction products in the liquid phase throughout the reaction.

U.S. Pat. No. 3,723,530 to Goetze et al. also discloses a process for preparing a mixture of alkanolamines by the liquid phase reaction of ethylene oxide and a large excess of ammonia. In this patent the mole ratios of ammonia to ethylene oxide are from 14:1 to 40:1. The patent describes the process as being capable of being run continuously, either isothermally or adiabatically. When operated continuously, the reaction is carried out in the liquid phase at temperatures in the range from 60° C. to 150° C. and pressures of 20 to 120 atm., and the monoethanolamine content of the product mixture generally does not exceed 70% by weight.

The preferred method for making alkanolamines is set forth in copending applications Ser. Nos. 247,061, filed Mar. 24, 1981, and 259,899, filed May 4, 1981. These applications disclose processes for preparing alkanolamines in which high yields of monoalkanolamines are obtained. The proceses involve the reaction of, e.g., ethylene oxide with a large excess of ammonia in a single supercritical fluid phase. The processes disclosed in said applications are capable of being run batchwise or continuously under isothermal or adiabatic conditions. When the process is operated as a continuous process, the desired reactor is of a design which provides for the minimization of product recycle and thereby maximizes the production of the desired alkanolamines, minimizing the formation of higher molecular weight alkanolamine products. The preferred process for making the alkanolamines involves reacting a homogeneous stream of a mixture of ethylene oxide and ammonia in a molar ratio of ammonia to ethylene oxide within the range between about 15:1 and about 50:1. The stream is maintained in a single, homogeneous, supercritical fluid phase by maintaining a temperature and pressure which creates such a phase. The temperature for effecting the supercritical fluid is that temperature which constitutes the minimum critical temperature for the fluid composition. Typically, the supercritical fluid phase has a density of at least 15 pounds per cubic foot. This supercritical fluid phase is maintained for a period of time sufficient to permit the reaction to proceed to completion and thus to form a product mixture containing predominantly monoethanolamine (frequently at least about 70 weight percent of the composition of the alkanolamines) and small amounts of the di- and triethanolamines.

In practicing this preferred process for making the alkanolamines, the temperature employed for carrying out the reaction between ethylene oxide and ammonia is preferably above the critical temperature of the reaction mixture. When maintained at that temperature, a single supercritical fluid phase is achieved within which the reaction between ethylene oxide and ammonia will occur. The reaction proceeds while the reaction mixture is maintained above its critical temperature to achieve the single supercritical fluid phase. If one increases the pressure of the reaction zone, then there will be a consequent increase in the reaction rate. An increase in pressure is reflected by an increase in the density of the supercritical fluid phase. The degree of increase in the density of the reaction mixture is only important as it relates to the reaction rate, but in terms of practicing the process for making the ethanolamines it is only necessary that the reaction mixture be maintained as a single phase supercritical fluid. In the typical case, the density of the single phase supercritical fluid will be at least 15 pounds per cubic foot (240 kg/m$^3$).

The reaction may be carried out under isothermal or, preferably adiabatic conditions. While no catalyst is required, the presence of a small amount of water in the reaction mixture has an advantageous catalytic effect. In the preferred embodiment, it is desirable to effect the reaction in a plug-flow type reactor by feeding a stream comprising ammonia and ethylene oxide to one end of a tubular plug-flow type reactor and withdrawing the effluent containing the desired alkanolamines from the other end thereof. It is also very desirable in the practice of the invention to maximize the plug-flow characteristics of the reactor so as to minimize any backmixing or recycling that might occur which could develop unwanted thermal gradients and undesirable reactions between ethylene oxide and ethanol-amine products.

In making the ethanolamines, it is preferred that a large excess of ammonia relative to the ethylene oxide be used in the reaction and to obtain yields of monoethanolamines of at least 65 weight percent, preferably at least 75 weight percent. In a typical practice of the invention in order to obtain these desirable yields of monoethanolamine, one may employ between about 15 to about 50 moles, and preferably between about 20 to about 35 moles, of ammonia for each mole of ethylene oxide.

As indicated above, the temperature at which the reaction between ethylene oxide and ammonia is carried out is important if one operates the reaction such that the reaction mixture is maintained in single supercritical fluid phase during the course of the reaction. As pointed out previously, the temperature should be above the critical temperature for the reaction mixture in order to achieve the supercritical fluid phase. The temperature should be above 130° C. and may be as high as 225° C. though the upper limit of the reaction temperature is not critical so long as the critical temperature of the reaction mixture is exceeded. In the most preferred embodiment, the reaction temperature is within the range from about the critical temperature of the reaction mixture, generally from about 130° C. to about 225° C. Under isothermal conditions, since the reaction is strongly exothermic, it is desirable to withdraw heat from the reaction mixture to keep the temperature approximately constant.

In cases where the reaction is to be carried out under adiabatic or nearly adiabatic conditions, the reactants are preheated to a temperature which is at least sufficient to effect an interreaction between the reactants, such as a temperature as low as 20° C. and higher. It should be understood that if one attempts to effect the reaction at such low temperatures that such will not occur with the reaction mixture being in a single supercritical fluid phase and therefore it will be necessary to utilize the exotherm of the reaction to achieve conditions which would bring the reaction mixture under supercritical fluid conditions as aforestated. However, in the desirable practice of this invention the reactant mixture is introduced at a temperature such that they achieve a supercritical fluid condition. Under such conditions, the reaction occurs rapidly with a strong exotherm. In the typical case, the reactant mixture is heated and introduced to the reaction zone at a temperature sufficient to achieve the supercritical fluid conditions instantly or rapidly. The pressure of the reaction zone, coupled with its temperature, should be such as to achieve the supercritical fluid state. Desirably, the pressure throughout the course of the reaction maintains the single phase supercritical fluid state. The pressures applied in the reaction of ammonia with ethylene oxide is within the range of about 2000 pounds per square inch absolute (psia) to about 5,000 pounds per square inch gauge (psia).

Though the reaction of ethylene oxide and ammonia under supercritical fluid conditions need not be carried out in the presence of any particular catalyst, it has been found advantageous as characterized in the aforementioned copending applications to effect that reaction in the presence of a small amount of water incorporated with the reaction mixture. It has been found that such a small amount of water has an advantageous catalytic effect on the reaction rate for forming ethanolamines though it does not appear to affect the yield of monoethanolamine in the product mixture. The amount of water which can be used to affect catalytic activity is not a critical amount, and typically only small amounts of water are utilized to effect this kind of result. In general from about 0.5% to about 5% by weight of water based on the weight of the reaction mixture may be utilized to catalytically induce the reaction. Though greater amounts of water may be desirable or useful to affect the aforementioned catalysis, such amounts need not be employed and indeed, in the typical case, they should be avoided to limit the energy requirements needed to separate water from the product mixture.

In this embodiment, before carrying out the reaction of ethylene oxide with ammonia, the process (as pointed out previously) is carried out continuously under isothermal or, preferably adiabatic conditions, in a plug-flow type reactor or a series of reactors which in combination achieve the results of a plug-flow type reaction system. A turbulent single directional flow of the reaction mixture through a plug-flow type reactor, under plug-flow type reaction conditions, results in the flow of the stream through the reactor with a minimum amount of backmixing and thermal stratification. This results in essentially eliminating hot spots in the reactor which will effect the reaction rates, product distribution, i.e., as between monoethanolamine, diethanolamine and triethanolamine, and reaction between ethylene oxide and product ethanolamines.

The Amination Reaction

The amination reaction employed in carrying out the process of this invention is not narrowly limited provided that the objectives of the invention are obtained. To that extent, one may employ the technology of Arne, Lichtenberger et al., Winderl et al., Johansson et al., Adam et al., Corr et al., Boettger et al., Habermann and LeGoff et al. to produce ethylenediamine from the product mixture derived from the reaction of ethylene oxide with ammonia, as hereinabove described, provided that in doing so the objectives of the instant invention are realized.

However, in the preferred practice of this invention, the amination process is carried out in such a manner as to favor the selectivity of the reaction towards the production of ethylenediamine. This is accomplished by utilizing the nickel-rhenium catalysts which are described in the aforementioned Best patent and U.S. Pat. No. 4,111,840, patented Sept. 5, 1978, to Best.

Broadly speaking, the objective of the amination reaction is to convert the products of the reaction of ethylene oxide and ammonia, which products contain, inter alia, monoethanolamine, diethanolamine and triethanolamine to ethyleneamines. In the typical practice of the invention, the amination reaction serves to convert such products to, inter alia, ethylenediamine. As mentioned above the reaction of ethylene oxide and ammonia produces a stream which contains essentially ammonia, monoethanolamine, diethanolamine and triethanolamine. The amount of ammonia in the product mixture is subject to the amount of ammonia which is utilized in the reaction with ethylene oxide. In the typical case the amount of ammonia which will be used will be vastly in excess of the stoichiometry of the reaction to produce the product mixture and therefore the available ammonia which is used in the reaction between ethylene oxide and ammonia will in large part be adequate for the subsequent amination reaction to produce the alkyleneamines. The aforementioned mixture of ammonia, monoethanolamine, diethanolamine and triethanolamine will comprise the continuous homogeneous fluid stream mentioned previously. The homogeneous fluid stream can be supplied directly to the amination reaction. In practicing the process of this invention there is provided with the homogeneous fluid stream additional monoethanolamine as described above and that additional amount of monoethanolamine with the homogeneous fluid stream when provided to the amination reaction will comprise the amination feed stream.

As mentioned previously, the amination feed stream is supplied to the amination zone at a pressure which is equal to or somewhat lower than the pressure of the homogeneous fluid stream. Consequently, the amination reaction zone is at a pressure which is essentially equivalent to the pressure of the amination feed stream as it exists when introduced to the amination reaction zone.

In the typical case the amination feed stream will be composed of the components of the homogeneous fluid stream, recycled monoethanolamine and, optionally, hydrogen and/or ammonia. In the preferred operation of the process of this invention the amination feed stream is supplied to the amination reaction as a single phase supercritical fluid stream. However, the pressure of that supercritical fluid stream will be less than the pressure of the continuous homogeneous fluid stream which is removed from the reaction between ethylene oxide and ammonia, even though the latter stream is also in the typical case a single phase supercritical fluid stream.

The amination zone comprises as an essential ingredient in order to effect the amination reaction a catalyst material which will convert the aforementioned amination feed stream into a stream containing ethyleneamines, preferably containing inter alia ethylenediamine. Such material effects the production of the ethyleneamines, as aforedescribed, preferably favoring the formation of ethylenediamine. Though the catalysts which are generally described in the prior art as capable of converting a mixture of ammonia and monoethanolamine in the vapor state to ethylenediamine may be utilized in the practice of this invention, the preferred catalyst is a solid material comprising nickel and rhenium on a support as described in the aforementioned Best patents. Such catalyst, characterized as having high activity and selectivity in amination processes, comprises rhenium and nickel impregnanted on a support material such as alpha-alumina, silica, silica-aluminas, kieselguhrs or diatomaceous earths and silica-titania in which the mole ratio of nickel to the rhenium is in the range of 2:1 to about 30:1 and the total nickel and rhenium metal present is in the range of 3 to 30 percent by weight of the support. Such catalysts are discussed at length in U.S. Pat. No. 4,123,462 and such disclosure for their manufacture is incorporated herein by reference, in particular that disclosure set forth in column 4, lines 24-34, starting at column 5, line 59, all of columns 6, 7, 8 and ending at line 23 of column 9, example 2, 3, 4, 5, 6, 7, 8, 9, 10, and 12. The same disclosure can be found in U.S. Pat. No. 4,111,840, patented Sept. 5, 1978, and that disclosure is also incorporated herein by reference.

The amination feed stream contains at least 70 weight percent monoethanolamine based on the total ethanolamines content, not more than about 30 weight percent diethanolamine, same basis, not more than 15 weight percent of triethanolamine, determined on the same basis, and the sum of diethanolamine and triethanolamine does not exceed 30 weight percent of the total ethanolamines content thereof. The amination feed stream also contains ammonia in an amount which is in stoichiometric excess of the alcoholic hydroxyl groups which are present in the amination feed stream. In the preferred case there is contained at least 10 moles of ammonia for each mole of ethanolamines present in the amination feed stream. In the most preferred embodiment there is provided at least 15 moles of ammonia from each mole of ethanolamine provided in the amination feed stream and the utilization of at least 20 moles of ammonia for each mole of monoethanolamine which is present in the amination feed stream being the most highly preferred embodiment. The amination feed stream may also possess a limited amount of water. The water that is present will typically be that which is provided as a result of the ethylene oxide-ammonia reaction. The water content in the amination feed stream may range between 0 weight percent to 10 weight percent, basis the weight of the amination feed stream and preferably the water content is kept between 0-5 weight percent, basis the total weight of the aminaion feed stream.

In further characterizing the amination feed stream, the preferred monoethanolamine content thereof is at least 90% of the weight of the total ethanolamines contained therein, while the diethanolamine content of the amination feed stream is typically at least 3% of the weight of the aforementioned total ethanolamines content. Usually the triethanolamine content of the amination feed stream is at least 0.5% by weight of the total ethanolamines content.

The reaction which involves the amination feed stream to produce ethyleneamines is accomplished in the amination zone. This zone contains the solid catalyst and has a temperature and pressure sufficient to cause the amination feed stream to react to form the ethyleneamines, such as ethylenediamine, etc. The amination zone contains the appropriate catalysts for the amination reaction, as described above, provided as a fixed bed, the amination feed stream, hydrogen and ammonia. When hydrogen and ammonia are not components of the amination feed stream in the appropriate proportions, they may be supplied separately as gases to the aminatin zone.

The hydrogen may be supplied to the reaction zone as a separate feed stream into the amination zone or as a component of the amination feed stream. Hydrogen serves the purpose of a promoter for the catalyst. When hydrogen is not provided in the reaction zone and the catalyst is a nickel-rhenium catalyst as described above, the catalyst life is greatly shortened and the rate of amine production is materially reduced. By providing hydrogen in the amination zone, the catalyst is continuously promoted to effectively cause the amination of the alkanolamines to produce the desired products. It is believed that hydrogen acts as a continuously supplied inert to keep available sites at the catalyst surface for the desired reaction between ammonia and the ethanolamines and preclude the stabilization of the catalyst sites by alkyleneamines and/or ammonia.

Inert gases can be supplied to the reaction such as nitrogen, helium, methane, and the like. Such inert gases can be utilized to help in the control of the reaction temperature and assist in maintaining the desired pressure conditions during the course of the reaction.

Suitable inert solid diluents for the catalyst can be any of the aforementioned support materials utilized in the manufacture of the catalyst and preferably is a material such as alumina, silicon carbide, silica, glass shot or balls, and the like. Such solid inert materials serve the purpose of adequately diluting the bed for the purpose of controlling gas flow characteristics within the catalyst bed as well as assisting in the control of the temperature occurring within the animation zone.

As mentioned immediately above, the catalyst is provided in the reaction zone in the form of a bed of particles. Typically such beds are supported upon distribution plates or screens which allow for the passage of gases or fluids through the bed. In this respect, the process is carried out utilizing standard fluid-solid heterogeneous catalytic techniques.

Also supplied to the amination zone is an amount of monoethanolamine in addition to that which is supplied to the amination feed stream from the homogeneous fluid stream. This monoethanolamine is provided to the amination zone in mixture with the amination feed stream, and therefore becomes a part thereof either immediately prior to the feeding of the amination feed stream to the amination zone or at some point further upstream of the amination zone.

As mentioned previously hydrogen is supplied as a promoter for the catalyst. The amount of hydrogen that should be present in the amination feed stream should be from about one mole percent to about 30 mole percent based on the total moles in the amination feed stream. Preferably the amount of hydrogen which is provided in the amination zone is from about 2 to about 15 mole percent based on the total moles in the amination feed stream.

The temperature of the amination zone in the usual case is selected based upon a temperature charactistic of the catalyst for effecting the amination reaction. When considering the nickel-rhenium catalyst mentioned above, this temperature is about 120° C. to about 225° C., preferably in a range of about 150° C. to about 215° C. It should be mentioned that in carrying out the process in its most desirable embodiment, the stream within the amination zone is under supercritical fluid or vapor phase conditions, preferably under supercritical fluid phase conditions as described above. Therefore, the pressure within the reaction zone should be correlated with the temperature so as to achieve either the supercritical fluid or vapor phase conditions. It is most desirable to avoid the presence of any liquid on the catalyst. That is, the catalyst should be essentially free of any liquid deposition on its surface. If such deposition occurs, it will very rapidly cause the dissolution of the catalyst on the surface of the support used with it and consequently the catalyst will become liquified and be carried away with the effluent from the amination zone. As that occurs, the catalyst within the zone will contain less and less of the desired nickel and rhenium, and consequently, its activity will decrease to such an extent that eventually it will no longer activate the amination reaction.

In carrying out this process, in a preferred embodiment utilizing a nickel-rhenium catalyst which also contains boron as described in the aforementioned Best patents, the pressure is in the range of about 1500–3000 psia, with the preferred pressure being approximately 2250 psia. When operating at such pressures the temperature is in the range of about 150°–215° C. and the fluid velocity through the amination zone is carried out at about 0.5–1.0 feet/min.

The amination reactor which provides the amination zone may be any reactor configuration ranging from a fixed bed tubular reactor to a backmixed fixed bed reactor. In view of the fact that the amination reaction does not provide a significant exotherm, it is not necessary for one to utilize a fluid bed reactor. However, one may utilize a fluid bed reactor if such is desired. One important feature of a reactor is that it should be designed to provide for a uniform flow distribution of the amination feed stream (and hydrogen, ammonia, and the like gases to the extent that such are not included with the amination feed stream) to the reaction zone. The better interdispersion of the various components of the amination feed stream (as well as hydrogen, ammonia and other gases supplied to the amination zone) better will be the overall effectiveness of the amination reaction.

After the fluids are removed from the amination zone, they are subjected to a variety of separation steps for the purpose of removing the various components contained therein. For example, the effluent fluid stream from the amination zone will be subjected to distillation to remove water, ethylenediamine, monoethanolamine (which will be recycled as described above), hydroxyethylpiperazine, aminoethylethanolamine, tetraethylenepentamine, diethylenetriamine, aminoethylpiperazine, piperazine, triethylenetetramine, diethanolamine and triethanolamine. Because of the vast difference between the boiling points of monoethanolamine, diethanolamine and triethanolamine, the separation of monoethanolamine from the composition is very readily obtained and an extremely pure stream of monoethanolamine can be produced by simple distillation. In the normal course, the monoethanolamine which can be obtained by distillation will contain at least 99 weight percent of monoethanolamine with extremely small amounts of piperazine, diethylenetriamine, aminoethylpiperazine, hydroxyethylpiperazine, and the like, being present.

High Pressure Separation

In a preferred embodiment of this invention, the homogeneous fluid stream which comprises the effluent from the reaction of ethylene oxide and ammonia is introduced to a high pressure separator which serves the purpose of producing an amination feed stream which is enriched in respect to its monoethanolamine content without creating a significant energy loss resulting from a large pressure reduction. In essence, what occurs is that the homogeneous fluid stream is passed to a simple high separator tank in which a modest phase separation occurs resulting in the removal from the tank of a gaseous stream which is richer in monoethanolamine than the homogeneous fluid stream which is provided to the tank. Withdrawn from the bottom of the tank is a stream which contains a smaller content of monoethanolamine. In a preferred embodiment of the invention, this high pressure separation is practiced as follows. The homogeneous fluid stream which is removed from the reaction between ammonia and ethylene oxide is passed as a supercritical fluid to admixture with the monoethanolamine recycle introduced at a temperature substantially below that of the homogeneous fluid stream. As a result, the temperature of the homogeneous fluid stream is reduced and the resulting stream that is formed from admixture with the recycled monoethanolamine is no longer in a supercritical fluid condition. That stream is thereafter passed to a heat exchanger and the temperature of the stream is raised to a temperature which allows the enriched amination feed stream which is taken from the high pressure separator tank to be again a supercritical fluid stream. For example, if the effluent from the ethylene oxide-ammonia reaction comprising the continuous homogeneous fluid stream is at 170° C., it will be cooled by recycled monoethanolamine which is at 45° C. to form a stream having a temperature of 143° C. which is no longer a supercritical fluid. That stream is thereafter heated to form an effluent from the high pressure separator tank having a temperature of 160° C. and further heated to a temperature of 180° C. and possessing the conditions of a supercritical fluid. It also follows that by introducing the recycled monoethanolamine into the fluid stream followed by high pressure separation that there is a loss of pressure from that at which the homogeneous fluid stream is at when taken as an effluent from the ethylene oxide gas-ammonia reaction. As described previously, that reaction is carried out at pressures within the range of about 2000 pounds per square inch absolute to about 5000 pounds per square inch absolute. For example, should the effluent from the ethylene oxide-ammonia reaction be at 3300 psi, it typically will be reduced to a pressure of about 2200 psi before it is fed to the high pressure separator tank and reheated through a heat exchanger to a temperature which achieves a supercritical fluid condition.

The high pressure separator tank is nothing more than a simple tank containing therein a demister pad at its upper area to remove any liquid components trapped in the volatile components removed from the upper portion of the tank. The liquid body which is created in the tank as a result of the phase separation occurring therein, will be removed from the bottom thereof and will be richer in diethanolamine and triethanolamine than is the homogeneous fluid stream minus any amount of monoethanolamine which had been added to such stream prior to its addition to the high pressure separator tank.

The monoethanolamine recycle which is provided can be an amount which is equivalent to the amount of monoethanolamine not converted in the amination zone to ethyleneamines. The monoethanolamine recycle can be introduced before or after the aforementioned high pressure separation, but at least in any case prior to the amination zone in admixture with the amination feed stream. If it is introduced prior to the amination zone to the components of the amination feed stream, then for the purposes of this invention, it is considered a part of the amination feed stream and to the extent that the previous discussion refers to a supply of an amination feed stream to the reaction zone, such additional monoethanolamine is considered a component part thereof. In the preferred practice of this invention, the monoethanolamine is removed from the product stream effluent from the amination zone before the removal of piperazine. This monoethanolamine recycle is reduced in temperature to about 25° C. to about 60° C. and has a purity as aforedescribed. The monoethanolamine is recycled back to a point in the reaction chain prior to, the high pressure separator to affect admixture with the homogeneous fluid stream as described previously. It is also possible to recycle the monoethanolamine stream subsequent to the high pressure separation step so that it is not necessary to reduce the temperature of the monoethanolamine prior to its reintroduction as a recycle stream into the ethanolamine feed going to the amination zone. In such a case, where there is effected monoethanolamine enrichment by the utilization of a high pressure separation step, as described above, then the homogeneous fluid stream is cooled by heat exchanger to a temperature low enough to take it from a supercritical fluid stream to a vapor-liquid stream which allows separation to occur in the high pressure separation tank.

The Polyamines Reaction

As indicated previously, the ethyleneamines which are produced in the amination reaction are at least in part fed to a separate reaction with at least ethylene dichloride by feeding such part of the ethyleneamines to a polyamines reaction zone where the ethyleneamines are caused to react with ethylene dichloride. The polyamines reaction zone may contain as an optional ingredient at least one of ammonia and water. The objective of the reaction in the polyamines reaction zone is to produce higher molecular weight polyethylene polyamines per se or as the hydrochloride, which polyethylene polyamines are higher in molecular weight than the ethyleneamines by at least an ethylene moiety. The reaction mixture in the polyamines reaction zone most desirably comprises ethylene dichloride, ethyleneamines such as (for illustration purposes only) ethylenediamine, piperazine, diethylenetriamine, tetraethylenepentamine, and the like, and the optional ingredients of ammonia, water, and inerts such as inert gases. The reaction is effected in the usual case in the absence of any catalyst.

The composition of the steam fed to the polyamines reaction zone typically contains at least 5% by weight of ethylene dichloride. The concentration of the ethyleneamines fed to the polyamines reaction zone is typically at least 5% by weight of the total mixture. Ammonia, being an optionally provided component of the reaction, may be present in an amount ranging from 0 to 80% by weight of the total reaction mixture fed to the polyamines reaction zone. Water, because it contributes to the reaction, is a favorable ingredient to have present in essentially all instances. Though it is classified as an optionally provided ingredient, water does benefit the reaction considerably and its presence is most desirably in an amount of at least 10% by weight of the total reaction mixture. Inerts such a nitrogen and methane can be provided as either sparging gases or mixing gases to enhance the overall performance of the reaction and their concentration is totally optional, such concentrations being sufficient to enhance the overall pressure conditions which are desired for the particular reaction being undertaken.

The presence of the ethyleneamines with or without ammonia in the reaction is dependent upon the type of products which one wishes to produce. It is to be understood that ammonia provides three active hydrogens and therefore is trifunctional with respect to reaction with ethylene dichloride. Primary amines which contain two active hydrogens are difunctional with respect to any reaction with ethylene dichloride and it follows that secondary amines are monofunctional. Tertiary amines are non-functional with respect to reaction with ethylene dichloride. Taken that into consideration, it is also important to bear in mind that the reaction rate of any of the hydrogens bonded to nitrogen is dependent upon whether any other hydrogen bonded to the nitrogen has already been reacted with ethylene dichloride. Once an ethylene amino group has been reacted with ethylene dichloride, the reaction rate of any remaining active hydrogen is substantially surpressed, consequently primary amino groups will react in the main monofunctionally with ethylene dichloride and secondary amino groups will react more sluggishly but also monofunctionally. It is to be noted that the hydrogen of piperazine is exceptionally reactive and will compete with primary amino groups for ethylene dichloride. With that in mind, it is apparent that the molar ratio of NH to ethylene dichloride is significant in determining the type of products produced when a variety of amines are allowed to react with ethylene dichloride. This molar ratio is generally under such circumstances a significant factor in providing the average molecular composition of the resulting reaction product. In addition, the conditions of the reaction such as temperature and pressure will also play an important role in determining the molecular weight distribution of the composition resulting from the reaction. Another factor which plays a significant role is the concentration of water in the reaction. In the typical case the amount of water present in the reaction ranges from 15 to 60% by weight of the total reaction mixture.

The polyamines reaction is carried out at a temperature between 50° C. and 225° C., preferably between 100° C. and 200° C. The process can be operated at pressures ranging from about atmospheric up to as high as 5000 psi, typically ranging from 200 psi to 3000 psi. Lower pressures are typically employed when the concentration of ethyleneamines predominates, such as when no ammonia is employed.

As stated previously an important consideration is the NH (that is the "amino" group) to ethylene dichloride mole ratio. The amino to ethylene dichloride mole ratio should be at least 2/1. In the preferred case the amino to ethylene dichloride ratio will be greater than 2/1 up to about 40/1. In the most preferred case this ratio should be from about 6/1 to 25/1.

Ethylene dichloride is essentially insoluble in water. In carrying out any reaction in which water is employed in the reaction, it is important that there be effected excellent mixing to achieve a degree of interdispersion of the reactants to allow the reaction to proceed in a desirable manner. The better one mixes the reactants during the course of the reaction the better will be the results of the reaction. In that respect, the molecular weight distribution of the products of the reaction will be more predictable leading to more uniform results.

Examples of ethylene amines derived from ethylene oxide and ammonia by way of the aforementioned continuous process and suitable to be fed to the polyamines reaction zone of this invention for the purpose of making higher molecular weight polyethylene polyamines include ethylenediamine (EDA), diethylenetriamine (DETA), triethylenetetramine (TETA), tetraethylenepentamine (TEPA) and mixtures thereof. Thus, it will be appreciated that the combination of the two processes, one being the continuous process for making ethylene amines from ethylene oxide and ammonia and the other being the continuous process for making polyethylene polyamines from ethylene amines derived from the first process, affords a great deal of flexibility in controlling the product distribution obtained from the overall process of this invention.

The polyamines reaction may be effective in any one of a number of known reactor types. In the preferred practice of the reaction, the reactants are intimately mixed and fed to a tubular reactor continuously. It is desirable under such process conditions that there be enough intermixing occurring during the course of the flow of the reactants through the tubular reactor that the degree of intermixing is at least maintained, desirably enhanced within the reactor, to thereby assure uniformity of reaction. This can be achieved by relying upon the formation of eddy currents during the course of the flow of the reactants through the tubular reactor which eddy currents cause a localized intermixture of the reactants to occur and reoccur during the course of flow throughout the length of the reactor. For example, such can be achieved by flowing the gas through the tubular reactor at a Reynolds Number of at least 30,000. A Reynolds Number of $4 \times 10^6$ is within a practical range for flow through a tubular reactor. Another desirable reactor, though not as preferred as the tubular type reactor, is a backmix reactor or a series of stirred tanks all operated continuously.

The reactants are provided to the reactor by predispersing them prior to their introduction to the reactor. The degree of dispersion of a reactant should be sufficient to assure upon entry to the reactor a sufficient level of interreaction and the level of intermixing which is maintained throughout the course of the reaction should be sufficient to achieve the uniformity of reaction which is desirable in order to obtain a reproducible reaction product mixture. However, it is not necessary that the reactants be predispersed before introduction to the reactor. Any one of the reactants can be supplied independently to a given reactor or each can be either fed as a co-fed product or independently fed downstream of the initially fed product to achieve incremental addition to thereby allow for a controlled molecular growth during the course of the travel of the reactants through a given reactor. This technique is particularly well suited for a tubular type reaction system.

Predispersion of the reactants may occur by simply placing the reactants in a stirrer which achieves rapid and thorough intermixing of the components of the reaction and feeding them mixed into a feed pump which enhance the interdispersion of the reactants. Mutually soluble components of the reaction such as ammonia, water and the ethyleneamines may be premixed followed by addition of the ethylene dichloride to that mixture and the combination intermixed in a feed pump and/or in other types of mixing devices. The same type of soluble stream may be fed to a venturi into which can be fed ethylene dichloride to effect intimate intermixing of the total reaction mixture. No single method of premixing the reactants is critical to the invention nor is any premixing even necessary. However, in the more favorable practice of the invention, premixing the reactants is preferred. The most important factor in achieving the uniform reaction is to provide for maximum intermixture of the reactants within the reactors during the course of the reaction. Such is the basic objective of the reaction system.

Coming now to the drawing, it illustrates a schematic flow diagram of an integrated process for carrying out this invention which includes the necessary separation of products from the amination reaction and the feeding of such products to reaction with ethylene dichloride in order to produce the polyethylene polyamines.

As shown in the drawing, ethylene oxide for the reaction is fed through line 16 into admixture with ammonia recycle fed through line 18. Makeup of ammonia is supplied through line 15 into line 18 on an as needed basis. The admixture of ammonia and ethylene oxide is achieved simply by connecting the respective lines for each and they are pumped by a high pressure feed pump (not shown) to heat exchanger 14.

In order to effectively utilize the energy resources of the process, the reaction mixture stream comprising ethylene oxide and ammonia are fed through a high pressure feed pump (not shown) to the tube side of a shell and tube heat exchanger 14, which is supplied with heat by passing the effluent from the catalytic reactor 36, that is, the effluent bottom fed through line 33 to the shell side of the heat exchanger 14. As a result, the ethylene oxide-ammonia reaction mixture is heated by passage through the tube side of the heat exchanger 14 to a temperature which is considered desirable for effecting the adiabatic reaction of ethylene oxide with ammonia under supercritical fluid conditions. For example, the feed stream to reactor 10 is brought to a temperature of about 136° C. and 3,000 psia. It is then fed into tubular reactor 10, having a length to diameter ratio of 40:1 and which contains in the entry port thereof a swirling device as described in copending application Ser. No. 259,899, filed May 4, 1981. The continuous homogeneous fluid stream removed from reactor 10 is in the form of a supercritical fluid. The temperature and pressure of the fluid is sufficient to effect the supercritical state, such as a temperature of 170° C. and a pressure of 3,000 psia. The pressure in the stream is controlled by a pressure reducing valve, not shown, and is fed to interconnect with the fluid from line 19. The fluid from line 19 can contain the monoethanolamine recycle or a mixture of monoethanolamine recycle and ammonia which is also recycled or simply ammonia from recycled ammonia. In the preferred practice of the invention, the monoethanolamine recycle is mixed with some of the ammonia recycle and the combination is fed through line 19 to effect admixture with the effluent from reactor 10, that is the homogeneous fluid stream. The control of ammonia recycle to line 19 is effected by valve 13 located in line 21. The control for monoethanolamine addition to line 21 is effected by valve 23 located in line 20. If it is desired to introduce the monoethanolamine recycle at a later stage, then valve 23 can be closed thereby diverting flow of the monoethanolamine recycle through line 27. In such a case, valve 25 will be opened and allow the flow of the monoethanolamine recycle to a later stage in the process scheme. The admixture of the monoethanolamine recycle and the homogeneous fluid stream is achieved upon contact of line 19 with line 11 through which the homogeneous fluid stream is passed. The admixture is thereafter fed to heat exchanger 12 for the purpose of further reducing the temperature of the mixed stream in line 11 to a desired temperature for the gas-liquid phase separation to be effected in high pressure separator 30. The temperature reduction is effected by both the reduced temperature of the monoethanolamine recycle stream, any ammonia which is also recycled therewith into line 19 and thereafter into line 11. Further reduction in the temperature is thereafter achieved by heat exchanger 12 to effect the desired temperature for effective gas-liquid separation under the conditions of high pressure which are existing in separator 30. The pressure in line 11 and separator 30 is controlled so as to effect, in coordination with the temperature therein, separation of the homogeneous fluid stream from reactor 10. The effluent vapor taken from the top of separator 30 is fed through line 34 to a heat exchanger (not shown) whereby to increase the temperature of the effluent stream which at this instance is characterized as the amination feed stream. By increasing the temperature, while maintaining a pressure of from about 1500 to about 2500 psi, and preferably about 2200 psia for the amination feed stream, the amination feed stream is converted into a supercritical fluid stream. This supercritical fluid stream is fed through line 34 into the top of amination reactor 36 which contains a fixed bed of rhenium-nickel catalyst containing boron supported upon a diatomaceous earth particulate support.

Alternatively, the amination feed stream may be advantageously fed through line 60 controlled by valve 55 into the bottom of amination reactor 36 so as to effect an upward flow of the amination feed stream through the catalyst bed contained therein during the amination reaction.

In order to provide the necessary hydrogen promoter to the reaction, hydrogen which is within the system is recycled through hydrogen compressor 24 into the upper portion of the high pressure separator 30 through line 22 and is thereafter carried with the amination feed stream through line 34, or alternatively line 60, into reactor 36.

The effluent from reactor 36 is passed into line 33, or alternatively line 45, and thereafter through the shell side of the heat exchanger used for preheating the ammonia-ethylene oxide reaction mixture as described previously, designated in the drawing as heat exchanger 31 for convenience sake. Heat exchanger 31 depicts the shell side of the same heat exchanger previously characterized as heat exchanger 14 which is chracterizing the tube side thereof. The reaction product effluent from reactor 36 is thereafter passed through line 35 into an ammonia flash tank 38 for the purpose of separating ammonia and hydrogen from the effluent liquid stream. The ammonia and hydrogen are taken off through line 28 and subsequently separated whereby the ammonia is fed through ammonia recycle compressor 26 and then into line 18 for subsequent recycle or it is passed to line 29 for eventual introduction into line 18, also for ammonia recycle, as described previously. The hydrogen is fed into a recycle compressor 24 so that the hydrogen can be recycled to separator 30 as described previously. The bottoms from flash tank 38 are fed through line 39 into which the bottoms from high pressure separator 30 are also fed by way of line 32 and the admixture is fed into a second flash separator, 37, for additional separation of ammonia to be recycled through line 18 by way of line 43 and ammonia recycle compressor 26. The bottoms from separator 37 are fed to an ammonia stripping still, 40, through line 41 for final removal of ammonia from the amine reaction product mixture. The bottoms from the still 40 is passed through line 42 into distillation column 50 maintained at a temperature sufficient to remove the water contained in the reaction through line 49. The heavies from the reaction are recovered from distillation column 50 through line 44 and passed to still 52 for the recovery of ethylenediamine by way of line 51. The heavies from that distillation are removed through line 54 into piperazine still 56 from which piperazine is recovered through line 57. The bottoms from that separation are removed through line 53 and passed to still 58 for the recovery of monoethanolamine which is recycled by way of line 20 for eventual addition to the homogeneous fluid stream either prior to or after the high pressure separator 30. The bottoms of that separation are passed from line 59 into a series of refining columns for recovering each of the various components of the stream.

The bottoms which are passed to line 59 are introduced into distillation column 61 which serves to separate the ethyleneamines from the ethanolamines. The bottoms from column 61 pass through line 63 into distillation column 67 which separates hydroxyethylpiperazine and aminoethylethanolamine from the bulk of the ethanolamines. See copending application Ser. No. 306,907, filed Sept. 29, 1981, for details on the most effective distillaton scheme for separating ethanolamine and hydroxyethylpiperazine. Aminoethylethanolamine is removed in distillation column 71 through line 73, and diethanolamine and triethanolamines passed through line 75 to distillation column 77. Diethanolamine is taken off through line 79 and triethanolamine is recovered via line 81.

The ethyleneamines drawn from column 61 through line 65 are fed to the ethyleneamines refining section hereinafter described.

Ethyleneamines thus produced in the integrated process comprising ethylene oxide-ammonia reaction and amination reaction are fed through line 202 into the ethylene dichloride process for making polyethylene polyamines. Line 202 is supplied with ethyleneamines from namifold (or supply tank) 200 which receives one or more ethyleneamines from lines 51, 62, 114, 95, 113 and/or 111, each controlled by the flow valves therein. The ethyleneamines fed through line 202 are introduced into line 208 which optionally combines it with ethylene-amines recycled in the ethylene dichloride reaction system. The ethyleneamines in line 208 are combined with line 207 which is used optionally for ammonia recycle and thereafter fed via line 206 into line 204 to effect mixture with ethylene dichloride. The mixture in line 204 is fed into lines 209 and 210 which thereafter feed tubular reactors 212 and 214, respectively, where the reaction to produce polyethtylene polyamines is effected. The effluents from the reactors 212 and 214 are removed by way of lines 216 and 218, respectively, and collected into line 217 to be fed into ammonia flash tank 220 from which ammonia is withdrawn by way of line 222 into ammonia recycle line 207. If the process is not carried out with ammonia present during the reaction, then the flash tank is bypassed and no ammonia recycle line is required. In such a case the valve in recycle line 207 is closed. The bottom from flash tank 220 is passed by way of line 224 into ammonia stripping still 226. Caustic is fed to the stripping still 226 at the upper portion of the column. Residual ammonia which is recovered is fed by way of line 228 into ammonia recycle line 207. The bottoms from column still 226 are recovered through line 230 and passed to evaporation system 232 which in a series of evaporators (not shown) which remove the salt in the product stream by way of a series of crystallization steps (not shown). Amines which are evaporated during that step are taken off through line 236 and introduced into the amines recycle. That step is optional. The major portion of the product stream which is essentially salt-free is removed by way of line 242 into salty residue flash tank 264. The water and ethylenediamine evaporated therein is passed by way of line 266 back to the evaporation system for water removal and recovery of the lower boiling ethylenediamine. Water is taken from the evaporation system by way of line 240. The lighter amine fractions separated in the evaporation system are passed by way of line 244 into distillation column 246 for recovery of lighter boiling ethyleneamines such as ethylenediamine (EDA) which are suitable for recycle. If no ethylenediamine recycle is employed, then the EDA may be sold and the recycle line 248 may be closed by valve 250. The heavier polyethyleneamines are recovered from the bottom of column 246 and passed by way of line 252 into distillation column 254 for the separation of piperazine (DEDA, an abbreviation used in the drawing for diethylene diamine, the synonym for piperazine.). Higher ethyleneamines are recovered from flash tank 264 and fed through line 268 into stripper 270 which provides for the recovery of diethylenetriamine and tetraethylenetetramine which are passed through line 272 to line 252 and treated in distillation column 254. The combination of the bottoms recovered in column 254 is fed by line 256 into distillation column 258 which provides for the recovery of high purity diethtylenetriamine by way of line 260. The bottoms from column 258 are collected in line 262 and fed into the ethyleneamines recovery system discussed previously. The bottoms from stripper 270 are fed by way of line 274 into distillation column 276 from which tetraethylenepentamine is removed by way of line 278. The bottoms from column 276 are passed by line 283 into low pressure flash evaporator 284 which causes the separation of tetraethylenepentamine from the higher boilers. The tetraethylenepentamine is removed by way of line 282 and combined with the same product from line 278, passed into line 280 which introduces the tetraethylenepentamine into line 262 for treatment in the ethyleneamines refining system. The higher boilers removed from the flash evaporator 284 are recovered in line 286. The combined polyethylene polyamines collected in line 262 are fed into line 85 thence to distillation column 83 where separation of tetraethylenepentamine from the other polyethylene polyamines is effected. The tetraethylenepentamine is removed from column 83 through line 87 and is distilled in distillation column 89. The tetraethylenepentamine is recovered as an overhead product. The bottoms from column 89 are fed by way of line 90 into admixture with the heavies recovered in line 110. The higher polyethylene polyamines removed from the top of column 83 are combined with the ethyleneamines in line 65 and the mixture is fed by way of line 91 into distillation column 93 from which diethylenetriamine is recovered by way of line 95. The bottoms from line 93 are passed through line 97 into distillation column 99 from which aminoethylpiperazine is recovered by distillation by way of line 113. The bottoms from column 99 are fed by way of line 100 into decolorizing tank 101. The decolorizing agent is fed to the stream in line 100 by way of recycle decolorizer line 107. Decolorization is effected in tank 101 and the treated product is removed by way of line 103 into flash tank 105 from which triethyltetramine is removed by way of line 111. The higher boiler residual products in tank 105 are removed by way of line 109 and a portion of it is recycled to line 107 and the remainder is fed into line 110 for combining with the products in line 90. The product removed from line 110 is thereafter recycled back to line 242 and reincorporated in the refining system. The highest boiling polyethylene polyamines will be ultimately recovered by way of line 286.

EXAMPLE 1

The reaction system and apparatus shown in the drawing and discussed above, comprising a tubular ethylene oxide/ammonia reactor, an amination catalytic reactor, a polyolmines reactor and associated equipment, is used in this run. In this run, a liquid ethylene oxide feed is mixed with a liquid ammonia-water mixture (98 percent $NH_3$, 2 percent water) to give an ammonia to ethylene oxide mole ratio of 30:1. The mixed ammonia/ethylene oxide feed after being preheated to 135° C. is pumped into reactor 10, which is a four stage adiabatic, tubular reactor having a 40:1 length to diameter ratio. The pressure in the reactor 10, is controlled to maintain the flowing stream in a single, swirling, supercritical fluid phase having an average reaction mixture density of 21.5 lbs/ft$^3$. The pressure at the outlet of the final reactor stage of reactor 10 is 3000 psig (204 atm.) and the temperature of the product mixture is 170° C. after a residence time within the reactor of about 20 minutes.

The homogenous product mixture stream from the ethylene oxide/ammonia reactor 10 contains about 95 mole percent ammonia, 1.9 mole percent water, 2.4 mole percent monoethanolamine, 0.4 mole percent diethanolamine and less than 0.1 mole percent triethanolamine. The homogeneous fluid stream in line 11 is depressurized to 2200 psig (150 atm.) and mixed with stream 19 which is a combination at a weight ratio of 1:0.76 of a monoethanolamine recycle stream containing 99 mole percent monoethanolamine and an ammonia recycle stream containing about 98 mole percent ammonia and 2 mole percent water and then preheated to a temperature of 155° C. before being fed to a high pressure separator 30 maintained at a pressure of 2200 psig (150 atm.). A recycle stream containing about 80 mole percent hydrogen and 20 mole percent ammonia is also fed to the high pressure separator 30 through line 22.

The overhead stream from the high pressure separator is heated to 170° C. to form a homogenous supercritical single phase fluid before being fed to the catalytic amination reactor 36. The overhead stream from the separator 30 contains about 7.2 mole percent hydrogen, 87.0 mole percent ammonia, 1.4 mole percent water, 4.3 mole percent monoethanolamine, 0.1 mole percent diethanolamine and less than 0.01 mole percent triethanolamine.

The amination reactor 36 is a vertical reactor containing a solid catalyst comprising 7.0% nickel—1.86% rhenium—1.44% boron on a silica-alumina support. The feed stream enters the bottom part of the reactor through line 60 and flows upward through the catalyst bed while being maintained in a single supercritical fluid phase at a temperature of 170° C. and a pressure of 2200 psi (150 atm.).

The effluent taken from the top of the amination reactor 36 through line 45 in a single phase supercritical fluid stream containing about 7.2 mole percent hydrogen, 85 mole percent ammonia, 3.1 mole percent water, 1.3 mole percent ethylenediamine, 0.1 mole percent diethylenediamine (piperazine), 0.1 mole percent diethylenetriamine, 2.6 mole percent monoethanolamine, 0.1 mole percent diethanolamine and less than 0.01 mole percent each of aminoethylpiperazine, aminoethylethanolamine, and triethanolamine. This stream is cooled to 150° C. and depressurized to 400 psia (27.2 atm.) before being fed through a flash separator 38 where unreacted ammonia and hydrogen are recovered for recycling back to the ethylene oxide-ammonia reactor 10 and high pressure separator 30 respectively. The liquid bottoms from the flash separator 38 contains about 70 mole percent ammonia, 12 mole percent water, 5.3 mole percent ethylenediamine, 0.4 mole percent piperazine, 10.5 mole percent monoethanolamine, 0.3 mole percent diethylenetriamine, 0.04 mole percent aminoethylpiperazine, 0.3 mole percent aminoethylethanolamine, 0.36 mole percent diethanolamine and less than 0.05 mole percent of other amine products. This stream is combined with the liquid bottoms from the high pressure separator 30 containing about 61 mole percent ammonia, 4.3 mole percent water, 24.7 mole percent monoethanolamine, 4.1 mole percent diethanolamine and 0.6 mole percent triethanolamine, depressurized to 225 psia (15.3 atm.) and heated to 80° C. in a flash separator 37, where about 80 percent of the remaining unreacted ammonia is removed and recycled to the ethylene oxide/ammonia reactor 10.

The liquid bottoms from the flash separator 37 is fed to an ammonia stripping still 40, a standard distillation column operating with a pressure of 50 psia to remove the remaining unreacted ammonia and about 40 percent of the water for recycle.

The bottom stream from the distillation column 40 contains about 24 mole percent water and 18 mole percent ethylenediamine, 1.3 mole percent piperazine, 1.2 mole percent diethylenetriamine, 0.1 mole percent aminoethylpiperazine, 0.1 mole percent hydroxyethylpiperazine in addition to 50 mole percent monoethanolamine, 1.0 mole percent of aminoethyl-ethanolamine, 3.5 mole percent of diethanolamine and less than 0.5 mole percent of triethanolamine. This stream is then separated by standard distillation techniques into component alkanolamines and alkylenamines for recovery or recycle. Monoethanolamine is recycled through line 20 to and mixed with the homogeneous fluid product mixture in line 11.

An ethylenediamine product stream obtained from the top of the distillation column 56 is then continuously fed to the polyamines reaction system through line 202. Unreacted ethylenediamine is continuously recycled to the inlet of the polyamines reactors which are twin reactors consisting of tube reactors 212 and 214 arranged in parallel each having a diameter length ratio of 1:1920. Thus, the inlet streams 209 and 210, which are a composite of ethylenediamine stream 202, ethylene dichloride feed stream 204, ethylenediamine recycle stream 208 and ammonia recycle stream 207, comprising 36.1% $NH_3$, 10.5% ethylene dichloride (EDC), 8.4% ethylenediamine (EDA), 44.1% $H_2O$ and 0.8% diethylenetriamine (DETA) are fed to the reactors 214 and 212 respectively. (The percentages are based on the weight of the total composition.) The inlet temperature is 140° C. and the effluent temperature is 165° C. The space time of the reactant feed is 20 seconds. The reactor effluent has the following composition (weight % based on the weight of the total effluent).

$NH_3$: 34.1%
EDC: 0.%
EDA: 7.0%
$H_2O$: 44.1%
Piperazine: 0.5%
DETA (diethylenetriamine): 2.4%
TETA (triethylenetetramine): 2.5%
AEP (aminoethylpiperazine): 0.5%
TEPA (tetraethylenepentamine): 0.8%
PEHA (pentaethylenehexamine): 0.2%

We claim:

1. A continuous process for the manufacture of polyamines which comprises the joining of (I) a continuous process for the manufacture of ethylene amines including ethylenediamine which comprises; (A) providing (1) a continuous homogeneous fluid stream under pressure, which stream comprises ammonia, monoethanolamine, diethanolamine and triethanolamine as produced by the direct reaction of ethylene oxide and ammonia in which the number of moles of ammonia substantially exceeds the molar concentration of alcoholic hydroxyl groups present in such streams; (2) a continuous recycle stream consisting essentially of monoethanolamine; (3) an amination zone comprising a solid amination catalyst; and (4) a separation zone for separating monoethanolamine from the amination product stream removed from the amination zone which monoethanolamine forms said recycle stream; (B) feeding said recycle stream under pressure to said fluid stream to form a continuous amination feed stream under pressure; (C) feeding the amination feed stream to the amination zone under sufficient pressure to assure flow through the amination zone and to form an amination product stream containing ethylenediamine therein; (D) separating monoethanolamine from the amination product stream to form said recycle stream; and (E) continuously recovering ethylenediamine from said amination product stream; wherein said amination feed stream contains at least 70 weight percent monoethanolamine, based on the weight of the ethanolamines therein; the moles of ammonia in the amination feed stream exceeds the molar concentration of alcoholic hydroxyl groups in said amination feed stream; and the amination feed stream contains at least a 5% increase in the concentration of monoethanolamine over that contained in said fluid stream; with (II) a continuous process for the manufacture of polyethylene polyamines which comprises; (A) continuously feeding at least a portion of the ethylene amines produced by said continuous process (I) and ethylene dichloride, and optionally ammonia and water, to a polyamines reactor maintained at an elevated temperature; (B) optionally continuously recycling at least a portion of the ethyleneamines coming out of said polyamines reactor to the inlet feed of said polyamines reactor; and (C) continuously recovering polyethylene polyamines from the product stream.

2. The process of claim 1 wherein said ethylene oxide-ammonia product mixture stream is in a single, supercritical fluid phase.

3. The process of claim 1 wherein the amination feed stream in the amination zone is a homogeneous fluid.

4. The process of claim 3 wherein the amination feed stream in the amination zone is in a single, supercritical fluid phase.

5. The process of claim 1 wherein the solid amination catalyst in the amination zone comprises nickel.

6. The process of claim 5 wherein the solid amination catalyst in the amination zone comprises nickel-rhenium on a support medium.

7. The process of claim 1 wherein said continuous amination feed stream contains hydrogen.

8. The process of claim 1 wherein the temperature of said polyamines reactor is maintained within the range of 50°–225° C.

9. The process of claim 1 wherein water concentration in the feed stream entering said polyamines reactor is at least 10% by weight.

10. The process of claim 1 wherein the amino group/ethylene dichloride molar ratio in the feed stream entering said polyamines reactor is in the range of 2–400.

11. The process of claim 1 wherein ammonia is substantially absent in the stream entering said polyamines reactor.

12. The process of claim 1 wherein the ethylene amine stream derived from said process (I) and fed to said process (II) comprises one or more of ethylenediamine, diethylenetriamine, triethylenetetramine and tetraethylenepentamine.

13. The process of claim 1 wherein the ethylene amine derived from said process (I) and fed to said process (II) consists essentially of ethylenediamine.

14. The process of claim 1 wherein the polyamine stream derived from said process (I) and fed to said process (II) comprises diethtylenetriamine as a primary component.

* * * * *